United States Patent [19]

Duhamel et al.

[11] Patent Number: 5,584,875
[45] Date of Patent: Dec. 17, 1996

[54] METHOD FOR MAKING VASCULAR GRAFTS

[75] Inventors: Raymond C. Duhamel, Chelmsford, Mass.; Stephen Eldridge, Milford, N.H.; Barbara Kelley; Brendan McCrea, both of Nashua, N.H.

[73] Assignee: C. R. Bard, Inc., Murray Hill, N.J.

[21] Appl. No.: 227,274

[22] Filed: Apr. 13, 1994

Related U.S. Application Data

[63] Continuation-in-part of Ser. No. 811,821, Dec. 20, 1991, abandoned.

[51] Int. Cl.$^6$ ............................................... A61F 2/06
[52] U.S. Cl. ........................... 623/1; 427/2.25; 427/560; 427/322; 427/338; 427/430.1
[58] Field of Search ............................. 427/2.25, 231, 427/565, 246, 338, 414, 420, 322, 560, 2.31, 430.1; 623/1

[56] References Cited

U.S. PATENT DOCUMENTS

| | | | |
|---|---|---|---|
| 724,810 | 4/1903 | Clauson-Kaas . | |
| 3,106,483 | 10/1963 | Kline et al. | 117/62.2 |
| 3,322,125 | 5/1967 | Kurtz . | |
| 3,400,719 | 9/1968 | Buddecke | 128/334 |
| 3,862,553 | 1/1975 | Schwemmer et al. | 68/15 |
| 3,982,543 | 9/1976 | Schmitt et al. | 427/2.24 |
| 4,047,514 | 9/1977 | Stephens | 350/164 |
| 4,082,507 | 4/1978 | Sawyer | 8/94.11 |
| 4,167,045 | 9/1979 | Sawyer | 3/1.4 |
| 4,193,138 | 3/1980 | Okita | 3/1.4 |
| 4,326,532 | 4/1982 | Hammar | 427/419.7 |
| 4,329,383 | 5/1982 | Joh | 427/303 |
| 4,416,028 | 11/1983 | Eriksson et al. | 3/1.4 |
| 4,441,215 | 4/1984 | Kaster | 3/1.4 |
| 4,530,855 | 7/1985 | Youngkeit | 427/175 |
| 4,613,517 | 9/1986 | Williams et al. | 427/2.28 |
| 4,664,658 | 5/1987 | Sawada et al. | 604/266 |
| 4,670,286 | 6/1987 | Nyilas et al. | 427/2 |
| 4,704,131 | 11/1987 | Noishiki et al. | 623/66 |
| 4,743,258 | 5/1988 | Ikada et al. | 623/1 |
| 4,747,848 | 5/1988 | Maini | 623/1 |
| 4,748,042 | 5/1988 | Linnecke et al. | 427/2 |
| 4,784,659 | 11/1988 | Fleckenstein et al. | 623/1 |
| 4,816,020 | 3/1989 | Kapadia et al. | 623/1 |
| 4,822,361 | 4/1989 | Okita et al. | 623/12 |
| 4,842,575 | 6/1989 | Hoffman, Jr. et al. | 600/36 |
| 4,845,791 | 7/1989 | Schwemmer et al. | 427/366 |
| 4,879,135 | 11/1989 | Greco et al. | 427/2 |
| 4,902,290 | 2/1990 | Fleckenstein et al. | 623/1 |
| 4,911,713 | 3/1990 | Sauvage et al. | 623/1 |
| 5,024,671 | 6/1991 | Tu . | |
| 5,037,377 | 8/1991 | Alonso | 600/36 |
| 5,061,738 | 10/1991 | Solomon et al. | 427/2.28 |
| 5,108,424 | 4/1992 | Hoffman, Jr. et al. | 427/2 |
| 5,120,833 | 6/1992 | Kaplan | 530/356 |
| 5,123,912 | 6/1992 | Kaplan et al. | 427/2 |
| 5,134,192 | 7/1992 | Feijen et al. | 427/2 |
| 5,192,308 | 3/1993 | Ostapchenko | 427/2 |
| 5,197,977 | 3/1993 | Hoffman, Jr. et al. | 427/2 |
| 5,246,451 | 9/1993 | Trescony et al. | 427/2.25 |
| 5,383,927 | 1/1995 | Degoicoechea et al. | 623/1 |
| 5,447,966 | 9/1995 | Hermes et al. | 523/113 |

FOREIGN PATENT DOCUMENTS 1173811  12/1969  United Kingdom .

OTHER PUBLICATIONS

Benslimane, S., et al., *Biomaterials*, 7:268–272 (1986).
Slimane, S. B., et al., *Eur. Surg. Res.*, 872:1–5 (1987).
Merhi, Y., et al., *biomaterials*, 10:56–58 (1989).
Domurado, D., et al., *J. Bioengineering*, 2(1–2):79–91 (1978).

(List continued on next page.)

*Primary Examiner*—Diana Dudash
*Attorney, Agent, or Firm*—Wolf, Greenfield & Sacks, P.C.

[57] ABSTRACT

A method for forming vascular graft prostheses is described. In particular, the method relates to determining the carrying volume of a gelable material to fill the interstices of a fabric prosthesis, applying that carrying volume of gelable material to the prosthesis, and crosslinking the gelable material to form uniform gel-coated prostheses having low porosity.

41 Claims, 3 Drawing Sheets

OTHER PUBLICATIONS

Warocquier–Clerout, R., et al., "*Advances in Biomaterials 6*", (Elsevier, NY) pp. 373–378.

Duval, J., et al., "*Advances in Biomaterials 6*", (Elsevier, NY) pp. 269–274.

Slimane, S. B., et al., *Biomater. Artif. Cells Artif. Organs*, 15 (2):453–481 (1987).

Guidoin, R., et al., *Transactions–Am. Soc. Artif. Internal Organs*, 29:290–295 (1983).

Sigot–Luizard, M., et al., *J. Biomed. Mater. Res.*, 18(8):895–909 (1984).

Guidoin, R., et al. *Biomater. med. Devices Artif. Organs*, 4(2): 205–224 (1976).

Guidoin, R., et al., *Ann. Thorac. Surg.*, 37(6):457–465 (1984).

Rumisek, J., et al., *J. Vasc. Surg.*, 4(2):136–143 (1986).

Ben Slimane, S., et al., *Eur. Surg. Res.*, 20(1):66–74 (1988).

Ben Slimane, S., et al., *Eur. Surg. Res.*, 20(1):18–28 (1988).

METHOD FOR MAKING VASCULAR GRAFTS

This application is a continuation-in-part of U.S. Pat. application Ser. No. 07/811,821, filed Dec. 20, 1991, now abandoned.

FIELD OF THE INVENTION

This invention relates to methods for fabricating vascular prostheses that are impregnated with gelled proteins.

Background of the Invention

The use of artificial grafts or prostheses to replace and repair portions of human blood vessels that have become damaged due to disease and injury is well known. Numerous attempts have been made to provide a prosthetic device that satisfies the requirements of biocompatibility, durability, and ease of use. These attempts have included implantation of blood vessels derived from donor humans and animals as well as synthetically fabricated prostheses.

Among the synthetic prostheses, knitted or woven fabrics have long been used to form tubular grafts. However, unlike natural blood vessels provided from donors, synthetic grafts must be fabricated in a manner which provides them with properties that sufficiently simulate natural blood vessels. In particular, a vascular prosthesis should be substantially impervious to blood loss even in patients that have been heparinized. This may be achieved by minimizing the permeability of the graft to water and biological fluids. The prosthesis should also have good surgical handling characteristics, have low thrombogenicity, be free from embolic complications, have no adverse affect on blood, have features that encourage fibroblastic ingrowth, and have intrinsic strength characteristics sufficient to maintain dimensional stability even after a prolonged period in vivo. In some cases it is also desirable that such prosthetic grafts remain pliable and preserved in a relatively dry state for extended periods prior to use. This condition enhances the storage life of the graft and thus enhances its convenience to the surgeon and the hospital.

As noted above, numerous attempts have been made using blood vessel grafts fabricated from knitted or woven cloth. Many of these attempts have used grafts formed simply from cylinders of woven or knitted polymeric cloth. During use, such grafts were exposed to the patient's blood and allowed to stand for a time sufficient to allow the blood to coagulate in the interstices of the graft and on its surface. Although this method provided the graft with a coating that was biologically compatible, it extended the time needed to complete the surgical procedure and, because of the surgeon-performed coagulation step, it introduced substantial variability into the quality of the graft prior to its implantation into the patient.

In response to the problems associated with the need to treat textile prostheses with the patient's own blood, numerous attempts to form grafts having a biocompatible, absorbable protein coating have been undertaken. For example, grafts treated with collagen or crosslinked albumin are well known in the art.

Typically, grafts having a crosslinked albumin coating have been made by preparing a solution of albumin containing a crosslinking agent such as glutaraldehyde or carbodiimide, immersing a fabric tube in the solution, squeezing excess solution from the graft either manually or by mechanical means such as rollers, and allowing the albumin to gel and crosslink. This method of providing a graft having a crosslinked albumin coating has a number of disadvantages.

In particular, if not enough coating material is applied, the interstices of the fabric graft will not be fully infiltrated with the gelled coating material, resulting in dry spots and voids in the completed prosthesis. Such dry spots or voids have a relatively high water permeability, and as such, become potential sites of leakage. On the other hand, if an excess of coating material is used, a significant amount of variability is once again introduced into the prosthesis. For example, there may be some areas on the prosthesis in which the gelled coating is thicker than in other areas. Such excess gelled material has the potential to flake off, possibly causing complications.

Accordingly, a need exists for a method for making a biocompatible vascular prosthesis impregnated with a gelled protein in a manner such that the resulting graft has a uniform coating of gelled protein, free from dry spots and voids, and also free from areas having excess coating material. A need also exists for the resulting, substantially uniform prostheses made by such method.

SUMMARY OF THE INVENTION

The present invention relates to a method for fabricating vascular grafts or prostheses containing a precise, predetermined amount of a gelled material within the interstices of the prosthesis fabric and on its surface. Such a method results in uniform grafts that are free of dry spots and voids, and are also free from areas of excess gel. The grafts are further characterized by low water permeability.

In particular, the present invention relates to a method for fabricating vascular prostheses which comprises the steps of providing a porous textile tube substrate, determining the carrying volume of the textile substrate for the specific gelable solution to be applied to the substrate, loading the substrate with the carrying volume of gelable solution, and allowing the solution to gel. The resulting graft contains a precise amount of gelled material within the interstices of the textile tube and on its surface, and is characterized by a low water permeability. In addition, the variability of water permeability and coating volume compared among multiple grafts is substantially lower than those among grafts made using the methods of the prior art.

The gelable material may comprise virtually any biocompatible, bioerodable polymer. For example, materials such as polysaccharides and glycosaminoglycans may be adapted for use with the invention. However, it is noted that among the biocompatible, bioerodable polymers adapted for use with the present invention, proteins and protein solutions are preferred.

The amount of gelable protein solution that is provided to a textile substrate to form a fully impregnated final graft which has the desired amount of protein can be determined experimentally and will vary depending upon the specific textile fabric used, the specific gelable protein, the concentration of the protein coating solution, and the like.

In another aspect of the invention, a vascular graft is prepared for impregnation with a desired impregnating material by a pretreatment step in which a surfactant is applied to the graft or the graft is exposed to ultrasonic energy. In the former case, the graft is immersed in a surfactant and then dried, thereby leaving a uniform coating of surfactant on the graft. In the latter case, a porous substrate is immersed in a liquid bath and exposed to ultrasonic agitation until the liquid thoroughly impregnates the substrate. The substrate is then dried to remove the liquid as well as any contaminants, such as oils and greases, that may have been present in the substrate. Preferably, the liquid is an alcohol, water, or a mixture of both, and the substrate is later impregnated with a gelable coating solution which is then gelled.

Loading of the textile substrate with the gelable coating solution can be achieved by a number of methods including wicking the solution into the substrate or dripping or spraying a precise amount of the solution onto the substrate, preferably while rotating the substrate. The resulting vascular prosthesis is well suited for implantation into a patient because it does not suffer from the problems associated with prostheses made using uncontrolled impregnation techniques.

Thus, it is one object of the present invention to provide a method for making a vascular prosthesis having a uniform coating of gelled material contained within the pores of the prosthesis and on its surface.

It is yet another object of the present invention to provide an improved method for applying a material such as a gelable protein solution to the surface of a prosthesis in a manner that results in the formation of a uniform protein coating.

It is still another object of the present invention to provide a method for making a vascular prosthesis that is free of dry spots or voids uncoated by gel.

It is a further object of the present invention to provide a method for pretreating a substrate for a vascular graft to improve the ability of a coating solution to fully wet the substrate.

It is yet another object of the present invention to provide a method for making a vascular prosthesis that is free of excess gel material.

It is a still further object of the present invention to provide a method for making a vascular prosthesis that is biocompatible, durable, and adapted for in vivo use over prolonged periods of time.

It is another object of the present invention to provide a vascular prosthesis that is biocompatible, durable, and adapted for in vivo use over prolonged periods of time.

It is another object of the present invention to provide a vascular prosthesis having a low water permeability.

It is yet another object of the present invention to provide a vascular prosthesis having an extended storage life prior to use.

It is an important feature of this invention that a preferred prosthesis can be consistently formed with repeatable properties. Such a prosthesis can be made in small or large numbers having substantially uniform properties, one to another.

These and other objects and features of the present invention will become apparent from the following detailed description which discloses multiple embodiments of the invention.

DETAILED DESCRIPTION OF THE INVENTION

Figure 1:
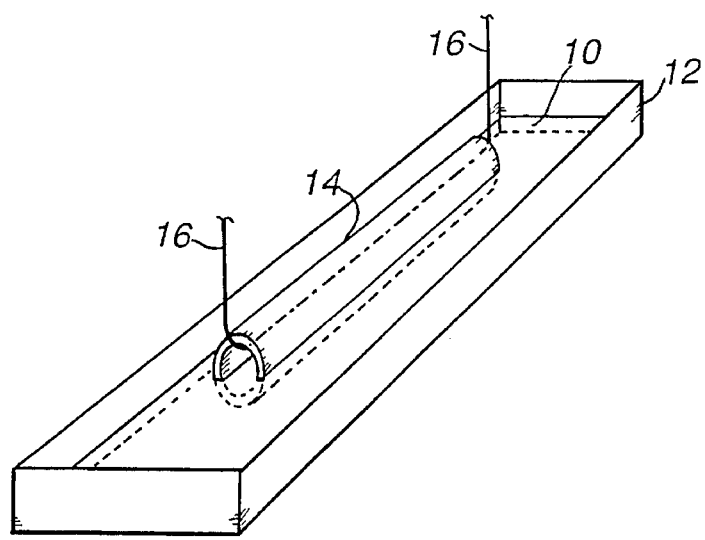
FIG. 1 is a schematic illustration of one method for coating a prosthesis with a solution of a gelable material.

The present invention relates to a method for making a prosthesis comprising a porous textile tube that is impregnated with a gel. The gel preferably comprises a material such as a protein that is provided to the textile tube in the form of a gelable solution. Unlike prior art methods in which excess amounts of gelable solution are supplied to the textile, the present invention provides the textile with a predetermined "carrying volume" of solution that corresponds to the maximum amount of solution needed to saturate the textile without dripping from the impregnated graft. Following impregnation of the textile tube with the gelable solution, the material is allowed to gel and crosslink, thereby resulting in a prosthetic graft having a predetermined quantity of gel contained within the interstices of the graft and on its surface. The gelable material is provided as a precise quantity to avoid problems associated with the use of either too much or too little material.

Prostheses made in accordance with the present invention exhibit uniform low permeability to blood when first implanted into a patient. Over time, however, the gelled coating erodes, thereby leaving a porous substrate, (i.e. the fabric tube), which serves as a foundation for biological ingrowth. The resulting graft is particularly well suited for long-term placement within a patient.

As used herein, the term "textile" is intended to refer to graft substrates formed of woven, nonwoven, and knitted fabrics. Any of a wide variety of textile fabrics are contemplated for use with the invention, however, fabrics formed of knitted polyethylene terephthalate fibers are preferred. It should be noted, however, that numerous other biocompatible polyester and non-polyester fabrics may be used as well.

Each of the above described textiles has the ability to absorb liquids such as the gelable coating solution. The amount of liquid that may be absorbed by a given textile is a function of a variety of variables including, but not limited to, the physical and chemical characteristics of the liquid, the size of interstices contained in the textile, the density, shape and spacing of the interstices, and the surface energy of the material forming the textile. As used herein, the term "carrying volume" is intended to refer to the maximum volume of gelable coating solution that can be held stably within the interstices of a given textile graft without dripping from the graft. As is discussed in detail below, the carrying volume of a given graft is precisely the maximum amount of material that can be wicked into a textile graft.

Textile prostheses that are immersed into excess volumes of coating solution and then removed carry an excess amount of gelable material that is allowed to drip from the graft or is removed using physical contact either manually or with a mechanical device such as a wringer. Such grafts contain amounts of material in excess of the carrying volume and exhibit the disadvantages described above.

The ability to provide a textile prosthesis with an amount of gelable coating material that corresponds precisely to the carrying volume for that graft offers the advantages of greater inter-graft uniformity in terms of porosity and the amount of coating material used, the elimination of processing steps required to remove excess coating material. Such grafts having a significantly lower and more uniform water permeability which, as discussed above, is a significant measure of the functionality of the graft.

Numerous gelable materials may be used in connection with this invention. In particular, proteins such as collagen, gelatin, fibrinogen and the like may be used, however, an albumin, such as human serum albumin is most preferred. Additionally, numerous other biocompatible, bioerodable polymers such as polysaccharides and glycosaminoglycans may be used as the gelable material as well.

The process for forming the graft includes the steps of providing a porous textile tube, determining the carrying volume of the tube for the specific solution of a gelable material that will be used to impregnate the pores of the substrate, impregnating the substrate with the carrying volume of the solution, and causing the solution to crosslink and gel. The final step may be achieved either by an affirmative act such as heating or providing a gelling initiator, or it may be achieved passively simply by allowing the solution to gel under the surrounding, ambient conditions. By providing the graft with the precise carrying volume of solution, dry spots and voids are avoided on the resulting graft, as are areas containing an excess amount of the gelled material.

Most preferably, the coating solution comprises a mixture of solutions of albumin and a crosslinking agent. Numerous crosslinking agents, including acrolin, formaldehyde and dialdehyde starches may be used, however, crosslinkers such as glutaraldehyde and carbodiimide are preferred. In one preferred embodiment, the coating solution includes a 25% solution of human serum albumin (USP grade human albumin for intravenous use) titrated to a pH of between approximately 5.6 and 5.8. If carbodiimide is used as the crosslinking agent, 1-ethyl-3-(3-dimethyl-aminopropyl) carbodiimide hydrochloride, referred to herein as EDC, is preferred. The EDC is diluted to a concentration of between approximately 11.8% to 12.4% in sterile water. The albumin solution is mixed with the EDC solution in a volume ratio of approximately 2.2:1 to provide the gelable solution used to impregnate the graft.

The above coating solution can be applied to a substrate comprising a knitted polyester tube, such as a tube of knitted polyethylene terephthalate fibers, having a 64 gauge reverse locknit structure using both 30 denier/20 filament and 40 denier/27 filament yarns. The carrying volume of such substrates is typically in the range of approximately 1.7–1.9 milliliters of the above-described coating solution per gram of fabric. Impregnating the substrate with the coating solution yields a graft having approximately 0.24–0.32 grams of gelled coating material per gram of fabric when the specified albumin solution is used. Of course, when other proteins or polymers are used, the weight of the gelled coating per unit weight of the fabric may be higher or lower.

A coating solution that yields a gelled coating having a weight of approximately 0.26–0.30 grams of coating material per gram of fabric is most preferred. It is noted that this value refers to the dry weight of the crosslinked protein end product.

The precise amount of coating material is preferably applied to the prosthesis by either a wicking method or a dripping or spraying method, each of which are described in detail below.

As depicted schematically in FIG. 1, in the wicking method, an amount of the gel forming solution 10, i.e. the protein and crosslinker, corresponding precisely to the carrying volume of the graft to be coated, is placed into an elongated, trough-like container 12. A substrate comprising a textile tube 14 is laid horizontally into the solution 10, allowing the gelable material to wick, via capillary action, from the container 12 into the tube to completely impregnate and saturate the tube with the carrying volume of gel forming solution that was originally contained within the trough. A wire 16 may optionally be positioned within the interior of the textile tube 14 to prevent the tube from twisting or curling during the wicking process. In the case of grafts having a relatively large cross-sectional diameter, the graft can be turned or rolled in the solution to allow contact between an upper surface and the solution, thereby accelerating the wicking process.

After the carrying volume of the gelable solution has been loaded into the substrate, the graft is removed from the trough and the protein in the gelable solution is allowed to gel and crosslink. Impregnation of the graft in this manner results in the presence of gelled protein which has infiltrated the interstices of the graft and is present on the graft surfaces as well. Since precisely the carrying volume of the gelable solution was provided to the substrate, the need to remove excess solution using manual or mechanical methods is eliminated, as is the presence of areas of excess gel. Likewise, the resulting graft is free of dry spots or voids which form regions of relatively high water permeability through the graft wall.

Figure 2:
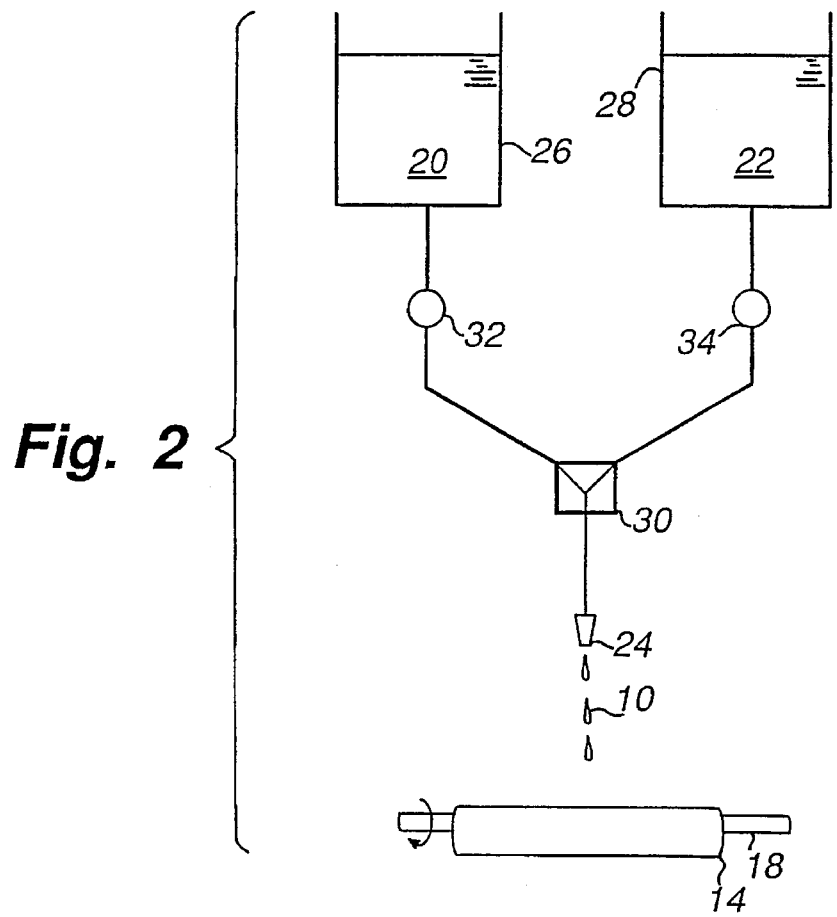
FIG. 2 is a schematic illustration of a second method for coating a prosthesis with a solution of a gelable material.

An alternative method for impregnating the graft is depicted in FIG. 2. In FIG. 2, a volume of a gelable protein solution 10 corresponding to the carrying volume of the substrate to be coated can be dripped or sprayed onto the porous fabric tube 14. In either case, it is important that the entire volume of solution is loaded into the substrate. Thus, the drip or spray apparatus must be configured in a manner such that no material is dripped or sprayed past the substrate. Preferably, the tube 14 is loosely positioned about a mandrel 18 and slowly rotated while a gelable mixture 10 of the protein 20 and the crosslinking agent 22 is dripped or sprayed from an orifice 24 onto the tube 14. In this case, the protein 20 is preferably mixed with the crosslinker 22 to form the gel forming solution 10 at some point prior to being dripped or sprayed onto the textile tube 14. The protein and crosslinker are preferably stored in separate containers 26, 28 and do not become exposed to one another until moments before the dripping or spraying when they are combined in a manifold 30 positioned between their respective containers 26, 28 and the orifice 24. The materials are supplied using precision pumps 32, 34 that are adapted to provide an amount of material for the mixing and coating procedures that corresponds to the predetermined carrying volume of the textile tube. As before, the resulting graft comprises a porous tube coated with gelled protein that has infiltrated into the interstices of the graft and is also present on the graft surface. The graft is free of areas of excess gelled material as well as dry spots or voids.

The above coating processes can be used in combination with numerous other process steps in the fabrication of a vascular prosthesis. In particular, prior to coating the graft tube with the coating solution, the tube optionally can be treated with a surfactant. Such a treatment alters the surface tension of the graft and allows the gelable solution to more uniformly coat and wet the fabric surface. Although numerous biologically compatible nonionic surfactants can be used during the fabrication of the prosthesis, a polysorbate surfactant such as Tween 80, (trademark of ICI United States, Inc.), in a methanol solution is preferred. Alternatively, polyethoxy ethanol and polyether alcohol surfactants, each available under the trade name Triton (trademark of Rohm & Haas) may be used as well.

By making the surface of the fabric graft more wettable, the surfactant allows the coating material to be more uniformly drawn into all surfaces and interstices of the graft, thereby eliminating the possibility of the formation of pockets of hydrophobic areas which are not impregnated or infiltrated with the coating. Application of the surfactant can be achieved simply by briefly immersing the graft substrate into the surfactant solution, removing the substrate from the solution, and allowing the substrate to dry prior to further processing.

Although not itself a surfactant, a solution of glycerol can be substituted for the surfactant solution. The glycerol also serves to lower the surface tension of the fabric substrate when allowed to dry onto the substrate.

Alternatively, the substrate can be exposed to ultrasonic agitation to render the surface more uniformly wettable. In this case, the substrate can be immersed into a bath consisting of an alcohol, such as methanol or ethanol, or water, or a mixture of alcohol and water. Once immersed, the substrate is sonicated by exposing it to ultrasonic energy. For example, the energy can be supplied at a frequency of approximately 47 kHz. Sonication is continued until the substrate is thoroughly impregnated with the bath solution for a time sufficient to obtain a cleaning effect from the bath and the agitating energy. Typically, treatment continues for at least about 30 minutes, however, treatment for at least about 1 hour is preferred. Following sonication, the substrate is removed from the bath, optionally rinsed with deionized water, and allowed to dry prior to further processing. The ultrasonic treatment may enhance the wettability of the porous substrate by removing contaminants, such as residual oils and greases, that may be present within the interstices of the substrate or it may expose hydrophilic groups that, in some circumstances, may be present in the substrate material. It is noted, however, that the invention is not intended to be limited to either theory as to the basis for enhanced wettability resulting from the sonication step.

It is noted that in each of the coating processes, the viscosity of the coating solution, the timing of mixing the protein with the crosslinking agent, the size and spacing of interstices of the substrate, the surface chemistry of the substrate material, and other factors all contribute to an overall set of parameters that must be considered if the coating process is to result in a graft having an empirically determined amount of gel distributed evenly and uniformly throughout the interstices of the graft.

Once the prosthesis is coated with the gelable mixture, such as an albumin/EDC mixture or an albumin/glutaraldehyde mixture as described above, it is allowed to crosslink. In the case of the albumin/EDC mixture for example, the prosthesis is allowed to crosslink for approximately 40–45 minutes at room temperature (between approximately 60° and 80° F.). Subsequently, each crosslinked prosthesis is soaked in a crosslinking inhibitor, preferably a 1.5% glycine solution, for at least about 30 minutes to arrest the crosslinking process. Although the aforementioned glycine solution is preferred, other suggested inhibitor solutions include other amino acids or low molecular weight amines. Following exposure to the inhibitor, the prosthesis is preferably soaked in two separate sterile water rinses for at least about 30 minutes each. These rinses serve to remove any remaining crosslinker and inhibitor from the prosthesis.

After the rinse steps, the prosthesis can be subjected to a leak test in which each graft is subjected to an inert gas such as nitrogen at a pressure of between about 30 and 120 mmHg for between 10 and 20 seconds. The samples that pass the leak test are then prepared for packaging.

Prior to packaging, the prostheses optionally can be treated to preserve them in a semi-dry state. This is achieved by soaking the prosthesis in a solution containing a humectant. The humectant solution may comprise virtually any biocompatible polyol, however, it preferably comprises a solution of approximately 23% glycerol in sterile water. Other humectant solutions such as solutions of sorbitol or trehalose may be substituted. This step serves to maintain the prosthesis in a flexible and pliable state and aids in the maintenance of a sterile packaging environment. Specifically, if the prosthesis is not treated with a humectant, it tends to dry out and become brittle. In contrast, preservation of samples with a glycerol solution maintains the samples in a flexible state and reduces the likelihood of contamination, since samples preserved in this manner can be sterilized at the point of manufacture and shipped in containers designed to insure sterility over extended periods of time.

Unlike many prior art prostheses in which the prosthesis is shipped and stored in a hard brittle state, (rendering it very fragile and requiring rehydration), prostheses treated with a humectant are durable and easily maintained in a semi-dry sterile condition for extended periods of time.

If the prosthesis is to be treated with a humectant, following the glycerol soak, the prosthesis can either be spun at a high speed or dried with an absorbent towel to remove excess glycerol. If the process has been carried out on an elongated segment of fabric, the prosthesis can be cut to any desired length prior to packaging.

Finally, the prosthesis is optionally exposed to humidity in a chamber having a relative humidity of 89–91% preferably at a temperature of 60°–80° F. for between 21 and 24 hours prior to packaging. Such a treatment in a humidity chamber also serves to maintain the prosthesis in a pliable and durable state.

As an alternative to preserving the prosthesis in a semi-dry state using a humectant, the prosthesis may be packaged and stored in a sealed, liquid-filled container. In this case, after treating the coated graft with a crosslinking inhibitor and rinsing, the graft is sealed into a package containing a sterile liquid. The graft may be stored in this package until it is used.

Preferred embodiments for the fabrication of vascular grafts will now be described in detail.

A knitted polymeric fiber graft as described previously (64 gauge reverse locknit structure using both 30 denier/20 filament and 40 denier/27 filament yarns) is soaked in a surfactant solution of 0.09–0.11% Tween 80 in methanol for 60–65 minutes at a temperature of 60°–80° F. The maximum bath loading is 0.06 grams of fabric per milliliter of surfactant solution.

A coating solution is prepared by providing a 25% solution of the USP grade human serum albumin and titrating the solution, using 1 N hydrochloric acid, to a pH in the range of 5.6–5.8. The result is a coating solution having a working concentration of between 22 and 23% human serum albumin in sterile water. This albumin solution should be prepared no more than 5 hours prior to use. EDC crosslinker is mixed in sterile water to a concentration of between approximately 11.8–12.4%. The crosslinker solution should be prepared no more than 36 hours prior to use. The crosslinking solution is mixed with the albumin solution and these are applied to the graft using the wicking method described previously. Of course, prior to application of the protein solution, it is necessary to determine the precise amount of that particular solution needed to saturate the particular fabric used as the graft.

Alternatively a 25%(w/v) solution of human serum albumin can be mixed with a 2.5%(w/v) solution of glutaraldehyde in a 2:1 volume ratio of albumin solution to glutaraldehyde solution and applied to the substrate in a total volume of 1.8 ml of mixture per gram of fabric.

Once applied to the graft, if using the concentration specified at a temperature of 60°–80° F. and EDC crosslinker, the albumin will gel within approximately 2–4 minutes and crosslink within approximately 40–45 minutes. If using the concentration specified at a temperature of 60°–80° F. and glutaraldehyde crosslinker, the albumin will gel within approximately 1–2 minutes and crosslink within approximately 20 minutes. Subsequently, the coated prosthesis is soaked in an inhibitor comprising an aqueous 1.5% glycine solution at a temperature of 60°–80° F. for between 0.5–24 hours, but preferably no more than 3 hours. The maximum bath loading in this step is 0.4 grams of fabric per milliliter of rinse solution. Upon removal from the inhibitor the graft is rinsed by soaking in sterile water in three successive baths each at a temperature of 60°–80° F. for approximately 30 minutes.

The rinsed grafts are subjected to a leak test in which they are tested using nitrogen at a pressure of approximately 120 mmHg for between 10 and 20 seconds. Grafts that pass the leak test are then treated with a humectant.

As noted previously, at this point, grafts can be either packaged in a sealed container containing a volume of a sterile liquid such as saline, or they can be treated with a humectant to allow the grafts to be packaged in a semi-dry state.

One embodiment of the humectant treatment involves soaking each graft in a glycerol solution containing 23–23.5% glycerol in sterile water. Preferably, the grafts are soaked in two separate and successive baths of the solution, each for a period of between 0.75–8 hours, with a total time of approximately 1.5 hours preferred. Each bath is maintained at a temperature of 60°–80° F. and has a maximum loading of approximately one milliliter of humectant solution per each 0.08 grams of graft material. The humectant treatment is completed by subjecting the grafts, at a temperature of 60°–80° F. to a humidity chamber having a relative humidity of 89–91% for 12–24 hours to achieve an equilibrium value of 0.6 to 1.0 grams of water per gram of fabric when the glycerol is present at a level of 0.3 to 0.5 grams of glycerol per gram of fabric. It is noted that while these values are considered to be optimum for grafts having crosslinked albumin, other water contents may be preferred depending upon the particular gel material present in the graft. Likewise, other methods known in the art for providing the graft with a humectant may be used.

Following the humectant treatment, the grafts can be packaged using conventional, packaging and sterilizing methods and materials. Prior to sterilization, the grafts can be stored at a temperature of between 40–46° F. for a period of approximately 10 days.

The resulting vascular prostheses are characterized by having a biocompatible, bioerodable coating that completely infiltrates the interstices of the graft and also covers the graft. The coating is characterized in that it is relatively uniform on each graft as well as being uniform among multiple grafts in terms of porosity and coating weight per gram of substrate material. In addition, the grafts made by the process described above are free of areas of excess or insufficient gelled material.

EXAMPLES

Example 1

Carbodiimide Crosslinking

A knitted polymeric fiber graft as described previously (64 gauge reverse locknit structure using both 30 denier/20 filament and 40 denier/27 filament Dacron™ yarns) was soaked in a surfactant solution of 0.10% Tween 80 in methanol for approximately 1 hour at room temperature.

A coating solution was prepared by providing a 25% solution of the USP grade human serum albumin and titrating the solution, using 1 N hydrochloric acid, to a pH of approximately 5.7. EDC crosslinker was mixed in sterile water to a concentration of approximately 12.1%. The crosslinking solution was mixed with the albumin solution (in a volume ratio of 2.2:1 albumin:EDC) and the mixture was applied to the graft using the wicking method described previously in which approximately 1.8 ml of solution was used per gram of fabric.

Once the solution has been fully wicked into the graft, it was maintained a room temperature and allowed to gel and crosslink. After approximately 40 minutes, the coated graft was immersed in a 1.5% glycine inhibitor solution for about 30 minutes. Subsequently, the graft was rinsed in sterile water for about 60 minutes.

The result was a graft having a uniform albumin coating on its surface and within the interstices of the fabric substrate.

Example 2

Glutaraldehyde Crosslinking

As before, a knitted polymeric fiber graft as described previously (64 gauge reverse locknit structure using both 30 denier/20 filament and 40 denier/27 filament Dacron™ yarns) was used. This graft was immersed in methanol and subjected to ultrasonic agitation for 1 hour. The graft was then rinsed with sterile water to remove any residual methanol.

A coating solution was prepared by providing a 25% solution of the USP grade human serum albumin. A glutaraldehyde crosslinker was mixed in sterile saline to a concentration of approximately 2.5%. The crosslinking solution was mixed with the albumin solution (in a volume ratio of 2:1 albumin:glutaraldehyde) and the mixture was applied to the graft using the wicking method described previously in which approximately 1.8 ml of solution was used per gram of fabric.

Once the graft was fully impregnated with the crosslinking solution, it was removed from the tray and allowed to crosslink for approximately 20 minutes at room temperature. Subsequently, the graft was soaked in a 1.5% glycine crosslinking inhibitor for about 90 minutes at room temperature and the rinsed by soaking in sterile water for about 90 minutes.

As in the case above, the result was a graft having a uniform albumin coating on its surface and within the interstices of the fabric substrate.

Example 3

Comparative Examples

The following examples compare manufactured lots of grafts made using the prior art method (referred to herein as the "Wringer/Spray" method) to grafts made using the methods described in the present application (referred to herein as the "Controlled Volume" method). In the designations of the grafts described below, a single number designator relates to a graft comprising a single tube having a diameter corresponding to the designator. Thus, a graft referred to as an 8 mm graft is a single tube having a diameter of 8 mm. Grafts referred to with two numerical designators comprise bifurcated Y-shaped grafts having a body portion intended to be connected to, for example, in the abdominal aorta and a pair of branches intended to be connected to the femoral arteries. Thus, a graft designated 16×8 mm describes a graft having a cylindrical body portion that is 16 mm in diameter bifurcated into two branches each having a diameter of 8 mm.

a) Wringer/Spray Method

Grafts made using the Wringer/Spray method were coated using a sequential application of glutaraldehyde crosslinker and albumin. Dry, crimped textile substrates were soaked in methanol and then immersed in a 2.5% glutaraldehyde solution. The grafts were passed between rollers to remove excess glutaraldehyde and then subjected to a spray of a 25% albumin solution. The amount of albumin solution used was greatly in excess to the carrying volume of each graft. Subsequently, the coated grafts were allowed to crosslink for approximately 20 minutes while being held horizontally and rotated. The rotation was intended to prevent pooling of excess solution on the graft. The crosslinked grafts were then rinsed in three glycine and two sterile water baths for approximately 30 minutes each. The grafts were manually cleaned while in the rinse baths to remove excess gel and then visually inspected. Grafts determined to have coating defects (i.e., uncoated void areas and the like) were discarded. The remaining grafts were then radiation sterilized and subjected to the water porosity test described below.

b) Controlled Volume Method

Under the controlled volume method of the present invention, dry, crimped textile grafts were soaked in methanol and then subjected to the sonication step described previously. The grafts were then contacted with a carrying volume of a premixed 25% albumin and a 2.5% glutaraldehyde solution in a 2:1 volume ratio. The carrying volume of the specific graft substrates for the coating solution had previously been determined to be approximately 1.8 milliliters of solution per gram of substrate. The carrying volume of the solution was wicked into each substrate. Subsequently, the solution was allowed to crosslink for approximately 20 minutes. Unlike the example above, rotation of the grafts during the crosslinking process was not necessary as there was no excess solution to pool or drip from the graft. The crosslinked substrates were then rinsed in three glycine and two sterile water baths for approximately 30 minutes each. Following the rinse steps, the resulting grafts were visually inspected and then subjected to a leak test using nitrogen at 120 mmHg as described above. The grafts were then radiation sterilized and subjected to a water porosity test.

c) Comparative Results

Coating Weight

Coating Weight is a measure of the amount of coating on a specified amount of graft. Data obtained from samples of 8 mm grafts is summarized below.

TABLE 1

| Graft Type | Sample Size | Average Coating Weight (g/g Fabric) | Coating Weight Range (g/g Fabric) |
|---|---|---|---|
| Wringer/Spray | 124 | 0.32 | 0.24–0.41 |
| Controlled Volume | 5 | 0.30 | 0.29–0.30 |

Figure 3A:
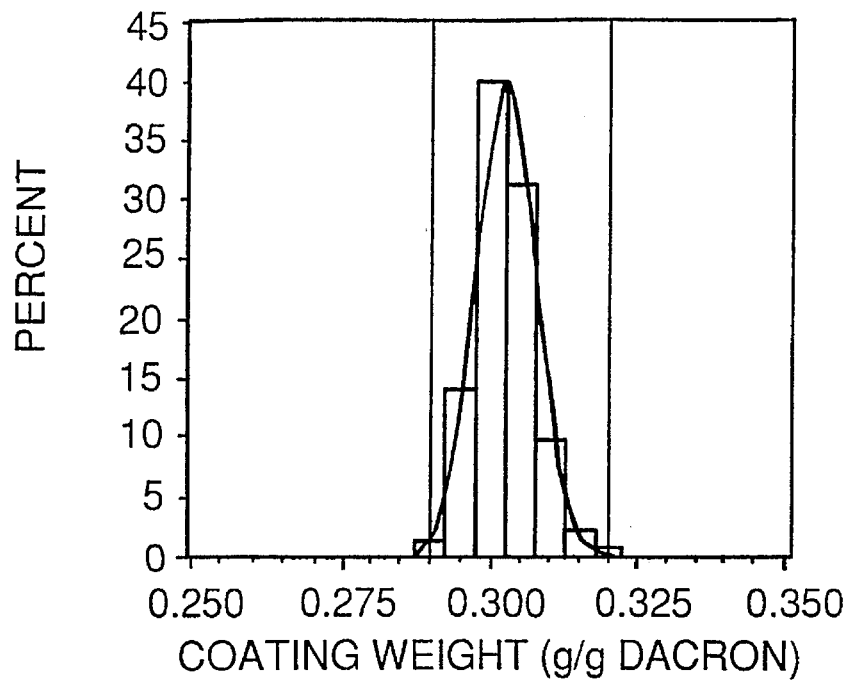
FIGS. 3a and 3b are graphs comparing coating weights for grafts made using the methods of the present invention and the prior art.
Figure 3B:
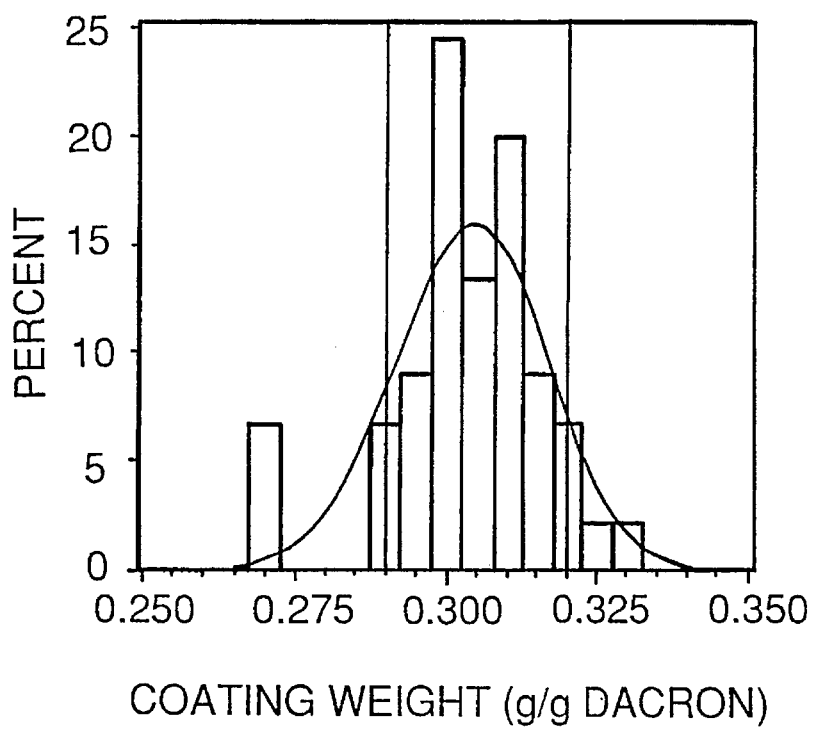

The coating data distribution for a large number of samples made using the controlled volume method and the Wringer/Spray method compared graphically in FIGS. 3a and 3b. In each, the data are plotted as frequency data for the indicated intervals and the estimated normal distribution is superimposed. Vertical lines represent the design specification limits of the controlled volume method (i.e., 0.290–0.320 g/g Dacron™ fabric).

FIG. 3a represents the coating weight distribution for grafts made using the controlled volume process. As may be seen in FIG. 3a, almost all grafts made using that process were contained within the design specification limits with a relatively narrow coating weight distribution between approximately 0.295–0.305 grams of coating per gram of fabric. In contrast, as may be seen in FIG. 3b, the coating weight distribution for grafts made using the Wringer/Spray method is much greater, with a far lower percentage of grafts coming within the design specifications. Thus, not only do grafts made using the Wringer/Spray method have a lower manufacturing yield rate, the weight distributions indicate that there is lower uniformity among those grafts than those made using the controlled volume method.

D. Porosity

Porosity of the grafts made using the Wringer/Spray and controlled volume methods is an indication of water permeability of those grafts. As noted above, it is desirable to maintain water permeability at a minimum. Porosity was determined using a procedure in which a 1 cm$^2$ patch of the graft is subjected to water maintained at an elevated pressure of approximately 120 mm Hg for one minute. The volume of water that passed through the sample area was collected and measured. Porosity is measured in units of cubic centimeters water transferred per square centimeter of graft per minute. Table 2 below summarizes porosity data for various size grafts made using the Wringer/Spray and controlled volume methods.

TABLE 2

| | POROSITY (cc/cm$^2$/min) | | | | | |
|---|---|---|---|---|---|---|
| GRAFT | Wringer/Spray Method | | | Controlled Volume Method | | |
| SIZE (mm) | Mean | Standard Deviation | No. of Samples | Mean | Standard Deviation | No. of Samples |
| 16 × 8 mm | 3.7 | 3.4 | 644 | 0.4 | 0.6 | 5 |
| 8 mm | 7.3 | 8.3 | 595 | 0.7 | 0.5 | 5 |
| 25 mm | 0.3 | 1.9 | 110 | 0.9 | 0.7 | 110 |
| 35 mm | 0.8 | 2.4 | 18 | 0.8 | 2.4 | 18 |

Figure 4:
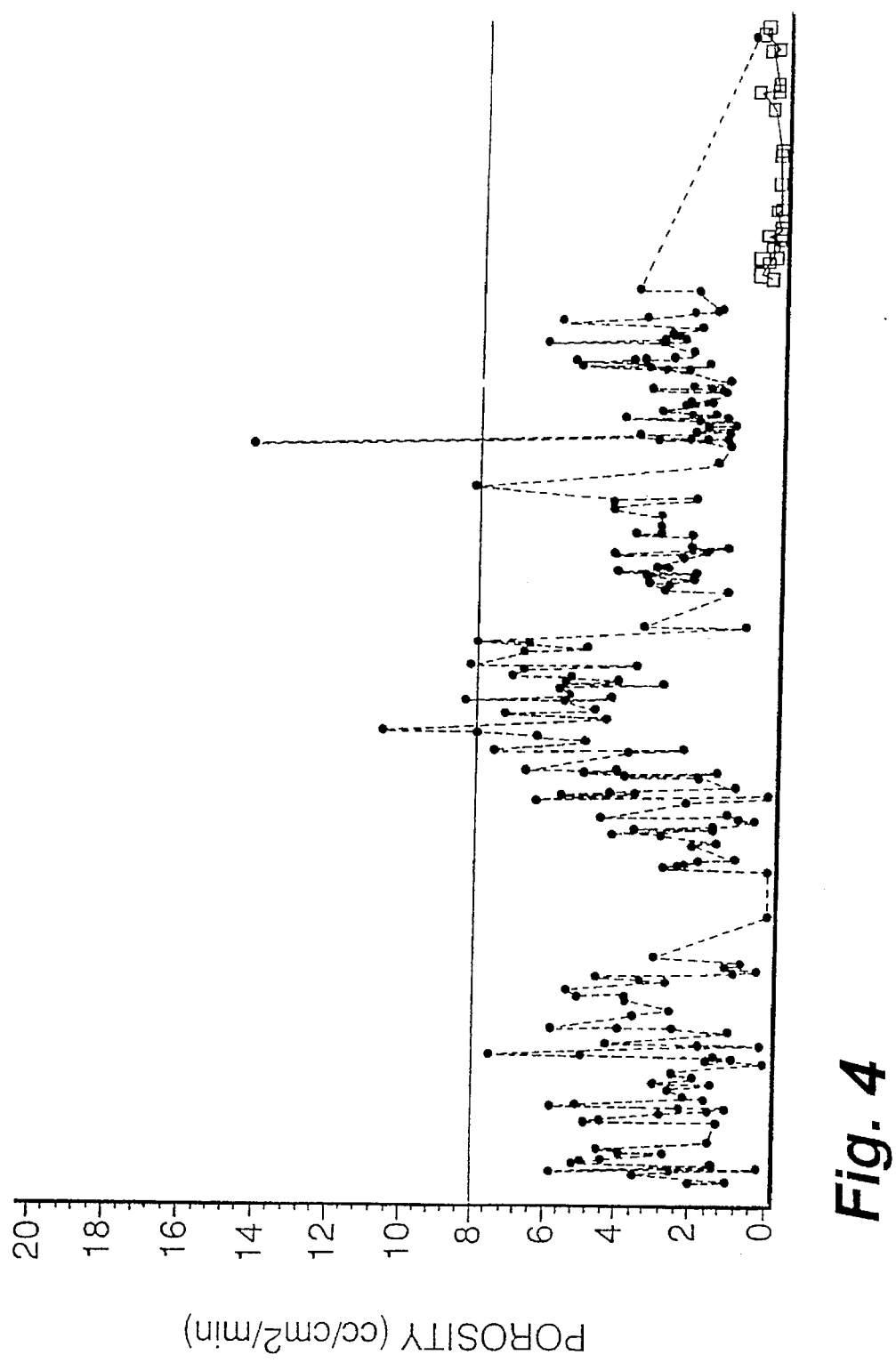
FIG. 4 is a graph comparing porosity of grafts made using the methods of the present invention and the prior art.

The improved porosity characteristics seen in grafts made by the controlled volume method is presented graphically in FIG. 4 which plots average porosity of of 16×8 mm grafts fabricated over a period of about 4 years. In FIG. 4, black b dots represent average porosity values for grafts made using the Wringer/Spray method and white squares represent average porosity for grafts made using the controlled volume method. The horizontal line at a porosity of 8 cc/cm²/min. represents the maximum design specification limit for porosity of the grafts. As may be seen in FIG. 4, grafts made using the controlled volume method have an average porosity that is well below the average porosity of grafts made using the Wringer/Spray method. As a result of the higher average porosity of many of the grafts made using the. Wringer/Spray method, a higher percentage failed to meet minimum product specifications, thereby resulting in a poor yield. In addition, controlled volume grafts are much more uniform in that the variation in average porosity among the various grafts fabricated at different times is much lower. For example, whereas the Wringer/Spray method grafts have a porosity that varies between approximately 0.1–14.4 cc/min, grafts made using the controlled volume method have an average porosity varying between approximately 0.1–0.8 cc/cm²/min.

Equivalents

Although the specific features of the invention are included in some embodiments and drawings and not in others, it should be noted that each feature may be combined with any or all of the other features in accordance with the invention.

Thus, the invention provides a method for fabricating a vascular prosthesis having a precise, predetermined amount of a gelled coating contained within the walls of the prosthesis.

It should be understood, however, that the foregoing description of the invention is intended merely to be illustrative thereof, that the illustrative embodiments are presented by way of example only, and that other modifications, embodiments, and equivalents may be apparent to those skilled in the art without departing from its spirit.

Having thus describing the invention, what we desire to claim and secure by Letters Patent is:

1. A method for fabricating a vascular prosthesis comprising the steps of:
    (a) providing a porous substrate comprising a textile tube having interstices,
    (b) providing a gelable material solution,
    (c) determining a carrying volume for the substrate of the gelable material solution,
    (d) loading the substrate with a volume of the gelable material solution equal to the carrying volume of the substrate, thereby filling the interstices of the substrate and providing a substrate containing gelable material, and
    (e) crosslinking the gelable material, thereby providing a substrate having a crosslinked gelled material contained within the interstices of the substrate and on its surface.

2. The method of claim 1 wherein the textile tube comprises a polyester fabric.

3. The method of claim 2 wherein the textile is a woven fabric.

4. The method of claim 2 wherein the textile is a knitted fabric.

5. The method of claim 1 wherein the gelable material is a bioerodable polymer selected from the group consisting of polysaccharides, glycosaminoglycans and proteins.

6. The method of claim 1 wherein the gelable material is selected from the group consisting of albumin, gelatin, collagen and fibrinogen.

7. The method of claim 1 wherein the substrate is loaded by wicking the carrying volume of the gelable material solution into the substrate.

8. The method of claim 1 wherein the substrate is loaded by dripping the carrying volume of the gelable material solution onto the substrate.

9. The method of claim 1 wherein the substrate is loaded by spraying the carrying volume of the gelable material solution onto the substrate.

10. The method of claim 1 wherein the crosslinking is achieved using a crosslinking agent.

11. The method of claim 10 wherein the crosslinking agent comprises a material selected from the group consisting of formaldehydes, dialdehyde starches, carbodiimides and glutaraldehydes.

12. The method of claim 11 wherein the carbodiimide comprises 1-ethyl-3-(3-dimethyl-aminopropyl) carbodiimide hydrochloride.

13. The method of claim 10 wherein the crosslinking agent is mixed with the gelable material prior to the loading step.

14. The method of claim 4 wherein the substrate having the crosslinked gelled material includes between approximately 0.24 and 0.32 grams of gelled material per gram of fabric.

15. A method for fabricating a vascular prosthesis comprising the steps of:
    (a) providing a porous substrate comprising a textile tube having interstices,
    (b) providing a gelable material solution,
    (c) determining a carrying volume for the substrate of the gelable material solution,
    (d) contacting the substrate with a surfactant prior to loading the substrate with the gelable material solution,
    (e) loading the substrate with a volume of the gelable material solution equal to the carrying volume of the substrate, thereby filling the interstices of the substrate and providing a substrate containing gelable material,
    (f) crosslinking the gelable material, and
    (g) contacting the substrate containing gelable material with a humectant.

16. The method of claim 15 wherein the textile tube comprises a polyester fabric.

17. The method of claim 16 wherein the textile is a woven fabric.

18. The method of claim 16 wherein the textile is a knitted fabric.

19. The method of claim 15 wherein the surfactant comprises a polysorbate surfactant, a polyethoxy ethanol surfactant, or a polyether alcohol surfactant.

20. The method of claim 15 wherein the substrate is immersed in the surfactant.

21. The method of claim 15 wherein the gelable material is a bioerodable polymer selected from the group consisting of polysaccharides, glycosaminoglycans and proteins.

22. The method of claim 15 wherein the gelable material is selected from the group consisting of albumin, gelatin, collagen and fibrinogen.

23. The method of claim 15 wherein the substrate is loaded by wicking the carrying volume of the gelable material solution into the substrate.

24. The method of claim 15 wherein the substrate is loaded by dripping the carrying volume of the gelable material solution onto the substrate.

25. The method of claim 15 wherein the substrate is loaded by spraying the carrying volume of the gelable material solution onto the substrate.

26. The method of claim 15 wherein the crosslinking is achieved using a crosslinking agent.

27. The method of claim 26 wherein the crosslinking agent comprises a material selected from the group consisting of formaldehydes, dialdehyde starches, carbodiimides and glutaraldehydes.

28. The method of claim 27 wherein the carbodiimide comprises 1-ethyl-3-(3-dimethyl-aminopropyl) carbodiimide hydrochloride.

29. The method of claim 26 wherein the crosslinking agent is mixed with the gelable material prior to the loading step.

30. The method of claim 20 wherein the resulting graft includes between approximately 0.24 and 0.32 grams of gelled protein per gram of fabric.

31. The method of claim 15 wherein the humectant comprises an aqueous solution of glycerol.

32. In the method of forming a vascular prosthesis which comprises a porous textile tube impregnated with a gelled material, the improvement which comprises determining a carrying volume for the porous textile tube of a gelable material solution, and impregnating in a single application the porous textile tube with the carrying volume of the gelable material solution.

33. The improvement of claim 32 wherein the material comprises a polysaccharide, a glycosaminoglycan or a protein selected from the group consisting of albumin, gelatin, collagen and fibrinogen.

34. The product produced by the method of claim 1.

35. The product produced by the method of claim 15.

36. A method for producing a vascular graft comprising a porous substrate impregnated with a biocompatible material, the method comprising the steps of:

(a) immersing the substrate in a liquid bath, (b) exposing the substrate to ultrasonic agitation, (c) removing the substrate from the bath, (d) drying the substrate, and (e) impregnating the substrate with a biocompatible material, by applying in a single application to the substrate a carrying volume for the substrate.

37. The method of claim 36 wherein the liquid bath comprises an alcohol, water, or a mixture of alcohol and water.

38. The method of claim 37 wherein the alcohol is selected from the group consisting of methanol and ethanol.

39. A method as claimed in Claim 1 further comprising the steps:

(f) immersing the substrate in a liquid bath, (g) exposing the substrate to ultrasonic agitation, and (h) removing the substrate from the bath, wherein the steps (f), (g) and (h) are performed prior to step (d).

40. The method of claim 36 wherein the biocompatible material is a gelable material.

41. In the method of forming a vascular prosthesis, which comprises a porous textile tube having interstices by impregnating the vascular prosthesis with gelled material, the improvement which comprises applying in a single application to the porous textile tube a carrying volume for the porous textile tube of a gelable material to fill the interstices, and causing the gelable material to form a gel within the interstices.

* * * * *